US009151815B2

(12) United States Patent
Miyazaki (10) Patent No.: US 9,151,815 B2
(45) Date of Patent: Oct. 6, 2015

(54) MAGNETIC RESONANCE IMAGING APPARATUS AND MAGNETIC RESONANCE IMAGING METHOD

(71) Applicants: KABUSHIKI KAISHA TOSHIBA, Tokyo (JP); TOSHIBA MEDICAL SYSTEMS CORPORATION, Otawara-shi, Tochigi (JP)

(72) Inventor: Mitsue Miyazaki, Mount Prospect, IL (US)

(73) Assignees: KABUSHIKI KAISHA TOSHIBA, Minato-Ku, Tokyo (JP); TOSHIBA MEDICAL SYSTEMS CORPORATION, Otawara-Shi, Tochigi (JP)

( * ) Notice: Subject to any disclaimer, the term of this patent is extended or adjusted under 35 U.S.C. 154(b) by 517 days.

(21) Appl. No.: 13/676,530

(22) Filed: Nov. 14, 2012

(65) Prior Publication Data

US 2013/0141094 A1 Jun. 6, 2013

Related U.S. Application Data

(63) Continuation-in-part of application No. 12/946,549, filed on Nov. 15, 2010, now Pat. No. 8,581,582.

(30) Foreign Application Priority Data

Nov. 15, 2011 (JP) .................................. 2011-250110

(51) Int. Cl.
*G01V 3/00* (2006.01)
*G01R 33/54* (2006.01)
(Continued)

(52) U.S. Cl.
CPC .............. *G01R 33/54* (2013.01); *A61B 5/0263* (2013.01); *A61B 5/055* (2013.01); *A61B 5/7285* (2013.01);
(Continued)

(58) Field of Classification Search
CPC ....................................................... G01R 33/54
USPC ......................................................... 324/309
See application file for complete search history.

(56) References Cited

U.S. PATENT DOCUMENTS 5,908,386 A * 6/1999 Ugurbil et al. ................ 600/410
6,271,665 B1 8/2001 Berr et al.
(Continued)

FOREIGN PATENT DOCUMENTS

CN 1543326 A 11/2004
JP 2001-149340 6/2001
(Continued)

OTHER PUBLICATIONS

Office Action dated Aug. 13, 2014, in CN 201180048821.7.
(Continued)

*Primary Examiner* — Rodney Fuller
(74) *Attorney, Agent, or Firm* — Nixon & Vanderhye P.C.

(57) ABSTRACT

A magnetic resonance imaging apparatus according to an exemplary embodiment includes a first imaging unit, an identifying unit, and a second imaging execution unit. The first imaging execution unit acquires, after applying a labeling RF pulse to blood flowing into the myocardium of a subject, multiple non-contrast MR data for which the time intervals between labeling and acquiring data are different by performing sequential imaging of an imaging area including the myocardium in each segment of a k-space for a given time interval. The identifying unit identifies a time interval taken by the labeled blood to reach a given position in the imaging area. The second imaging execution unit sets the identified time interval and, after applying a labeling RF pulse to the blood flowing into the myocardium of the subject, acquires non-contrast MR data by imaging the imaging area including the myocardium.

10 Claims, 9 Drawing Sheets

(51) Int. Cl.
*G01R 33/563* (2006.01)
*A61B 5/00* (2006.01)
*A61B 5/026* (2006.01)
*A61B 5/055* (2006.01)
*G01R 33/483* (2006.01)
*G01R 33/56* (2006.01)

(52) U.S. Cl.
CPC ...... *G01R 33/5635* (2013.01); *G01R 33/56366* (2013.01); *A61B 5/0555* (2013.01); *G01R 33/4833* (2013.01); *G01R 33/5608* (2013.01); *G01R 33/56325* (2013.01)

(56) References Cited

U.S. PATENT DOCUMENTS

| | | | |
|---|---|---|---|
| 6,295,465 B1* | 9/2001 | Simonetti | 600/413 |
| 6,564,080 B1 | 5/2003 | Kimura | |
| 6,618,605 B1* | 9/2003 | Wolff et al. | 600/410 |
| 6,782,286 B2 | 8/2004 | Miyazaki | |
| 6,801,800 B2 | 10/2004 | Miyazaki et al. | |
| 7,047,060 B1* | 5/2006 | Wu | 600/410 |
| 7,412,277 B1 | 8/2008 | Saranathan et al. | |
| 7,545,142 B2 | 6/2009 | Alsop | |
| 7,579,834 B2 | 8/2009 | Yui | |
| 7,613,496 B2 | 11/2009 | Miyazaki et al. | |
| 7,623,901 B2 | 11/2009 | Kanazawa | |
| 7,647,086 B2 | 1/2010 | Miyazaki et al. | |
| 8,581,582 B2* | 11/2013 | Miyazaki | 324/309 |
| 9,008,753 B2* | 4/2015 | Messroghli | 600/413 |
| 2003/0160612 A1* | 8/2003 | Yablonskiy et al. | 324/309 |
| 2003/0184291 A1* | 10/2003 | Rehwald et al. | 324/307 |
| 2004/0049106 A1 | 3/2004 | Kanazawa | |
| 2008/0061780 A1 | 3/2008 | Yamada et al. | |
| 2009/0005670 A1 | 1/2009 | Ichinose et al. | |
| 2009/0143666 A1 | 6/2009 | Edelman et al. | |
| 2009/0148020 A1 | 6/2009 | Sugiura | |
| 2010/0085051 A1 | 4/2010 | Littmann et al. | |
| 2010/0277172 A1* | 11/2010 | Takizawa | 324/309 |
| 2011/0071382 A1 | 3/2011 | Miyazaki et al. | |
| 2011/0080170 A1 | 4/2011 | Miyazaki | |
| 2011/0133735 A1* | 6/2011 | Yokosawa et al. | 324/307 |
| 2012/0108946 A1* | 5/2012 | Kuhara | 600/410 |
| 2014/0159720 A1* | 6/2014 | Markl et al. | 324/309 |

FOREIGN PATENT DOCUMENTS

| | | |
|---|---|---|
| JP | 2001-252263 | 9/2001 |
| JP | 2004-024637 | 1/2004 |
| JP | 2005-531352 | 10/2005 |
| JP | 2006-198411 | 8/2006 |
| JP | 2009-028525 | 12/2009 |
| JP | 2011-083592 | 4/2011 |

OTHER PUBLICATIONS

Zun, et al., "Assessment of Myocardial Blood Flow (MBF) in Humans Using Arterial Spin Labeling (ASL): Feasibility and Noise Analysis," *Magnetic Resonance in Medicine*, vol. 62, pp. 975-983 (2009).

Nishimura, et al., "Considerations of Magnetic Resonance Angiography by Selective Inversion Recovery," *Magnetic Resonance in Medicine*, vol. 7, pp. 482-484 (1988).

Miyazaki et al., "Nonenhanced MR Angiography", *Radiology*, 2008, vol. 248, No. 1, pp. 20-43.

U.S. Appl. No. 12/722,875, filed Mar. 12, 2010, Yamashita.
U.S. Appl. No. 12/763,643, filed Apr. 20, 2010, Miyazaki.
Office Action dated Jan. 28, 2013 in U.S. Appl. No. 12/946,549.

* cited by examiner

CINE IMAGE #1
BBTI=$T_0$

CINE IMAGE #2
BBTI=$T_0+\Delta$

CINE IMAGE #3
BBTI=$T_0+2\Delta$

CINE IMAGE #4
BBTI=$T_0+3\Delta$

CINE IMAGE #5
BBTI=$T_0+4\Delta$

CINE IMAGE #6
BBTI=$T_0+5\Delta$

MAGNETIC RESONANCE IMAGING APPARATUS AND MAGNETIC RESONANCE IMAGING METHOD

CROSS-REFERENCE TO RELATED APPLICATIONS

This application is a continuation-in-part (CIP) of application Ser. No. 12/946,549 filed on Nov. 15, 2010, the entire content of which is hereby incorporated by reference in this application. This application is based upon and claims the benefit of priority from Japanese Patent Application No. 2011-250110, filed on Nov. 15, 2011, the entire contents of all of which is incorporated herein by reference.

FIELD

Exemplary embodiments relate to a magnetic resonance imaging apparatus and a magnetic resonance imaging method.

BACKGROUND

Magnetic resonance imaging (MRI) is an imaging method in which nucleus spins of a subject placed on a static magnetic field is magnetically excited by using a high frequency (RF) signal of a Larmor frequency and an image is reconstructed from a magnetic resonance (MR) signal generated in accordance with the excitation. In the filed of magnetic resonance imaging, non-contrast MRA (magnetic resonance angiography) is known as a method of obtaining blood flow images without using a contrast agent.

DESCRIPTION OF EMBODIMENTS

Detailed Description

A magnetic resonance imaging apparatus according to an exemplary embodiment includes a first imaging unit, an identifying unit, and a second imaging execution unit. The first imaging execution unit acquires, after applying a labeling RF pulse to blood flowing into the myocardium of a subject, multiple non-contrast MR data for which the time intervals between labeling and acquiring data are different by performing sequential imaging of an imaging area including the myocardium in each segment of a k-space for a given time interval. The identifying unit identifies, on the basis of the acquired multiple MR data, a time interval taken by the labeled blood to reach a given position in the imaging area. The second imaging execution unit sets the identified time interval as a corresponding parameter of a pulse sequence and, after applying a labeling RF pulse to the blood flowing into the myocardium of the subject, acquires non-contrast MR data by imaging the imaging area including the myocardium.

Figure 1:
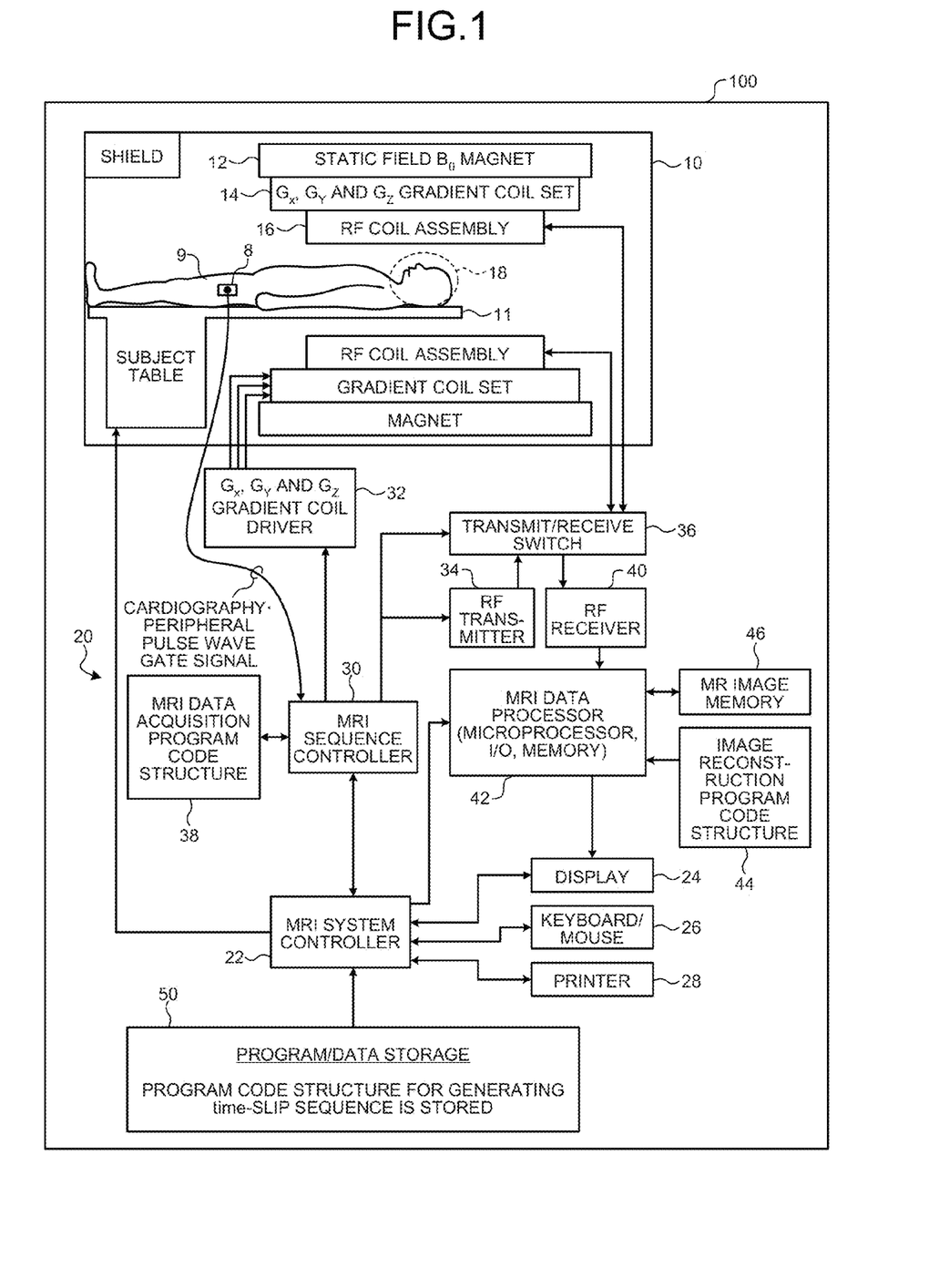
FIG. 1 is a schematic block diagram of an MRI system according to an embodiment.

The MRI (magnetic resonance imaging) system 100 shown in FIG. 1 includes a gantry 10 (shown in cross-section) and various related system components 20 interfaced therewith. At least the gantry 10 is typically provided in a shielded room. One MRI system 100 depicted in FIG. 1 includes a substantially coaxial cylindrical arrangement of a static field $B_0$ magnet 12, a $G_x$, $G_y$, and $G_z$ gradient coil set 14 and an RF (radio frequency) coil assembly 16. Along the horizontal axis of these cylindrically-arrayed elements, there is an imaging volume 18 shown as encompassing the head of a subject 9 supported by a subject table 11.

An MRI system controller 22 has input/output ports connected to a display 24, a keyboard/mouse 26 and a printer 28. As will be appreciated, the display 24 may be of the touch-screen variety so that it provides control inputs as well.

The MRI system controller 22 interfaces with an MRI sequence controller 30. The MRI sequence controller 30 controls $G_x$, $G_y$ and $G_z$ gradient coil drivers 32, as well as an RF transmitter 34 and a transmit/receive switch 36 (if the same RF coil is used for both transmission and reception). As those in the art will appreciate, one or more electrodes 8 may be affixed to the subject to provide ECG (electrocardiogram) signals and/or peripheral pulse wave gating signals to the MRI sequence controller 30. The MRI sequence controller 30 has access to suitable program code structure 38 for executing available pulse sequences to generate MR images by using operator inputs and/or system inputs defining particular sequence parameters.

The MRI system 100 includes an RF receiver 40 providing input to an MRI data processor 42 so as to create processed image data to be output to the display 24. The MRI data processor 42 may be configured for access to an image reconstruction program code structure 44 and to a MR image memory 46 (e.g., for storing MRI data derived from processing in accordance with the exemplary embodiments and the image reconstruction program code structure 44).

FIG. 1 also gives a generalized depiction of a MRI system program/data storage 50. Program code structures stored in the MRI system program/data storage 50 (e.g., for generation of time-SLIP images and cine images, operator inputs for the generation, etc.) are stored in computer-readable storage media accessible to the various data processing components of the MRI system. As those in the art will appreciate, the program storage 50 may be segmented and directly connected, at least in part, to various ones of the processing computers of the system 20 having most immediate need for program code structures stored as described above in their normal operation (i.e., rather than being commonly stored in and connected directly to the MRI system controller 22).

Indeed, as those in the art will appreciate, the depiction of FIG. 1 is a very high-level simplified diagram of a typical MRI system with some modifications so as to practice exemplary embodiments to be described hereinbelow. The system components can be divided into various logical collections of "boxes" and typically include numerous digital signal processors (DSP), microprocessors, special purpose processing circuits (e.g., for fast A/D conversions, fast Fourier transforming, array processing, etc.). Each of those processors is typically a clocked "state machine" wherein the physical data processing circuits progress from one physical state to another upon the occurrence of each clock cycle (or predetermined number of clock cycles).

Not only does the physical state of processing circuits (e.g., CPUs (central processing units), registers, buffers, arithmetic units, etc.) progressively change from one clock cycle to another during the operation, the physical state of associated data storage media (e.g., bit storage in magnetic storage media) is transformed from one state to another during operation of such a system. For example, at the conclusion of an MRI reconstruction process, an array of computer-readable accessible data value storage sites in physical storage media will be transformed from some prior states (e.g., all uniform "zero" values or all "one" values) to a new state. In such a new state, the physical states at the physical sites of such an array vary between minimum and maximum values to represent real world physical events and conditions (e.g., the tissues of a subject over an imaged volume space). As those in the art will appreciate, such arrays of stored data values represent and also constitute a physical structure. In other words, when such arrays are sequentially loaded into instruction registers and executed by one or more CPUs of the MRI system 100, a particular sequence of operational states occurs and a particular structure of computer control program codes transferred into the MRI system 100 is structured.

The exemplary embodiments described below provide improved ways to acquire and/or process data and generate and display MR images.

As MRI techniques, ASL (arterial spin labeling) for assessing myocardial blood flow without using a contrast agent is known. ASL is an imaging method of obtaining perfusion images by magnetically labeling the blood with RF pulses and using the labeled blood as a tracer. For example, the MRI system acquires control images for which the labeled blood does not contribute, acquires tagged images for which the labeled blood contributes by applying inversion pulses as an example of labeling pulses, and performs a difference processing on the acquired images. The tissues made still by the difference processing are canceled, so that the MRI system can obtain only images of blood components flowing into the imaging area. Regarding ASL, see, for example Zun, et al., "Assessment of Myocardial Blood Flow (MBF) in Humans Using Arterial Spin Labeling (ASL): Feasibility and Noise Analysis," Magnetic Resonance in Medicine, 62:975-983 (2009). Here, a two-dimensional ASL sequence is used to examine the tag on/off signal difference in the myocardium (with and without stress perfusion).

In addition, a time-SLIP (spatial labeling inversion pulse) method is known as MRI techniques. The time-SLIP technique is an imaging method of depicting a fluid flowing into or flowing out of an imaging area by labeling the fluid in a position independent of the imaging area and increasing or reducing the signal value of the fluid flowing into or flowing out of the imaging area. For example, the MRI system applies a time-SLIP pulse after a given wait time interval from a synchronization signal (e.g., R wave). The Time-SLIP pulses include an area non-selective inversion pulse and an area selective inversion pulse and on or off can be set for the area non-selective inversion pulse. When the fluid flowing into (or flowing out of) the imaging area is labeled by using the area selective inversion pulse, the intensity of the signal of the part that the fluid reaches after BBTI (black-blood time to inversion) time interval increases (decreases when the area non-selective inversion pulse is off). Regarding this time-SLIP technique, see, for example, application Ser. No. 12/763,643 filed Apr. 20, 2010. In this related application, a non-contrast cardiac perfusion time-SLIP technique is used to observe tagged (or marked) blood flow distribution by selecting an appropriate BBTI time interval.

Here, selection of an appropriate BBTI parameter value (hereinafter, "BBTI value") is critical in the time-SLIP technique. This is because, if the selected BBTI value is not appropriate, the "tagged" blood flow bolus may not reach the imaged ROI (region of interest) or may have already passed the ROI by the time MR data is acquired. Selecting an appropriate BBTI parameter value is difficult. This is because the BBTI value varies from subject to subject and varies even for the same subject depending upon heart rate and/or other subject-specific conditions.

With the angiography using the time-SLIP technique incorporating a variably positionable cine sub-sequence, the MRI system 100 according to the exemplary embodiment can alleviate and/or eliminate the problem in that selecting an appropriate BBTI value is difficult. Specifically, in order to find a myocardial perfusion signal difference in a high temporal resolution, the MRI system 100 according to the exemplary embodiment uses a 2D cine sequence to examine the signal intensity changes of the myocardium during desired cardiac phases (e.g., diastole). To examine signal changes in cardiac phases using flow-out, the MRI system 100 can use 2D time-SLIP technique with balanced SSFP (steady state free precession).

In particular, in an exemplary embodiment incorporating a cine sub-sequence (e.g., bSSFP or FFE (fast field echo) of two dimensions (e.g., one spatial dimension and one time dimension) or three dimensions (e.g., two spatial dimensions and one time dimension)), the MRI system 100 can discretionarily select a range of BBTI values for a given pulse sequence. For example, the duration of a segmented cine sub-sequence incorporated within the pulse sequence using the time-SLIP technique (hereinafter, time-SLIP sequence) can be controlled (e.g., by the operator or the MRI system 100). Similarly, for example, in the exemplary embodiment, the recovery time after the cine subs-sequence (e.g., recovery time before a new data acquisition cycle) and any desired initial triggering delay (e.g., any delay subsequent to a cardiac triggering event selected before one or more RF tagging RF pulses are applied) can be controlled.

After acquiring data using the variably positionable cine sub-sequence in a data acquisition cycle in the time-SLIP sequence, the MRI system 100 according to the exemplary embodiment can automatically perform any required image subtraction processing or other processing/analysis of acquired signals (e.g., with alignment between images). Preferably, RF tag "on" and tag "off" parameters can be preselected by the operator (or system) so that the MRI system 100 can thereafter automatically perform multiple pulse sequences before performing necessary image differencing operations.

The MRI system 100 according to the exemplary embodiment eventually can provide indications of blood perfusion signal intensity changes within the imaged myocardium that is displayed and/or stored and/or exported to a remote system or a remote site. The MRI system 100 provides an identified one of the MRI cine image frames acquired using the time-SLIP sequence incorporating the cine sub-sequence or images acquired by executing another time-SLIP sequence. Because another time-SLIP sequence is determined by previously identifying the most appropriate MRI cine image frame, another time-SLIP sequence is executed by using an appropriate BBTI value.

A time-SLIP sequence incorporating a cine sub-sequence may include, for example, the following cases: (a) one area-selective inversion pulse is applied upstream of the ROI so as to effect a flow-in angiography, or (b) an area non-selective inversion pulse and an area-selective inversion pulse are applied to the ROI so as to effect a flow-out angiography. Alternately setting on/off of the area selective inversion pulse makes subtraction for outputting the blood vessel easy.

In a time-SLIP sequences of the exemplary embodiment, there are three time dimensions that can be controlled (e.g., an initial triggering delay, the duration of a segmented cine sub-sequence, and a recovery time). On the other hand, in scanning where the area selective inversion pulse is alternately turned on/off, only the initial triggering delay and the duration of the cine sub-sequence may be selectable (e.g., by an operator and/or MRI system programming). It is preferable that the alignment between multiple images of the same ROI be carefully performed (e.g., so as to compensate for motion artifacts between cine image frames).

By using time-SLIP sequence with an incorporated segmented cine sub-sequence, the MRI system 100 according to the exemplary embodiment can depict signal changes during the subject's cardiac cycle (regardless whether the flow-in angiography with only a single area selective inversion pulse is used or a flow-out angiography with an area selective inversion pulse and an area non-selective inversion pulse are used). In the flow-in angiography, the MRI system 100 applies an area selective inversion pulse to the myocardium. The myocardium signal strength then decreases with increasing BBTI time interval during a time-SLIP sequence. In the flow-out angiographic approach, an area selective inversion pulse and an area non-selective inversion pulse are applied to an upstream portion of the myocardium. The myocardium signal strength then increases with increasing BBTI during a time-SLIP sequence. In the method of alternately setting on/off the area selective inversion pulse (hereinafter, "on/off alternate approach"), the myocardium signal strength increases with increasing BBTI time interval. The on/tag off alternate approach helps to eliminate background signals and observe blood flow into the myocardium.

The MRI system 100 according to the exemplary embodiment obtains the BBTI value in the cine sub-sequence with the efficient signal intensity change as an efficient BBTI value candidate possibly used in the subsequent time-SLIP sequence. The subsequent time-SLIP sequence is a time-SLIP sequence not incorporating a cine sub-sequence (a different desired sequence is used). In addition, The MRI system 100 according to the exemplary embodiment can use a cine image frame (that can be used to determine the most optimum BBTI value) can be used as a myocardial perfusion image.

For example, as an initial time-SLIP sequence incorporating a cine sub-sequence, the MRI system 100 performs relatively quick and efficient 2D time-SLIP sequence so as to identify the appropriate BBTI value. Thereafter, the MRI system 100 according to the exemplary embodiment performs a lengthy 3D time-SLIP sequence not incorporating a cine sub-sequence for multiple times over multiple slices so as to depict a three-dimensional image of the myocardium.

Figure 2:
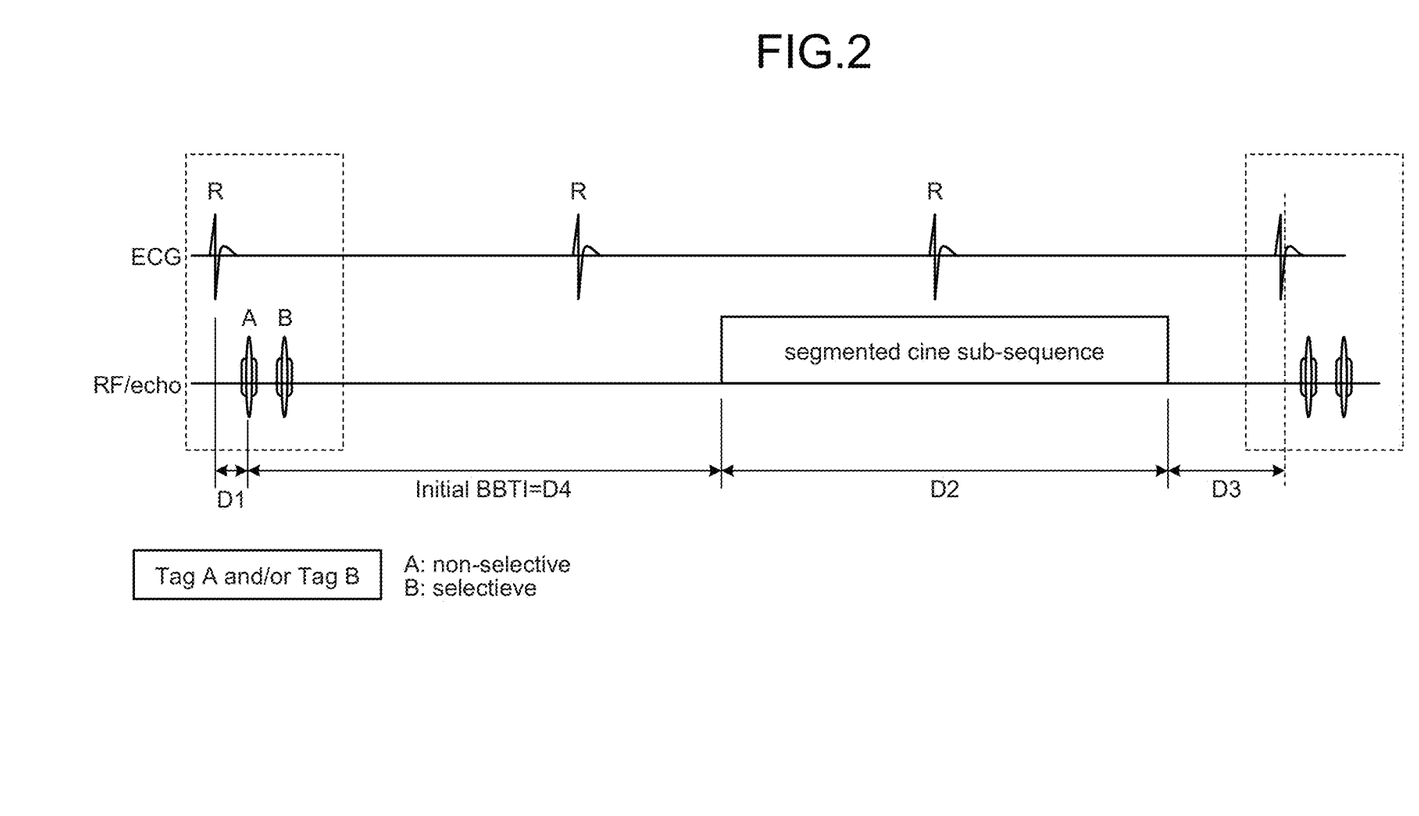
FIG. 2 is a chart illustrating a time-SLIP (spatial labeling inversion pulse) sequence according to the exemplary embodiment.

FIG. 2 is a chart illustrating a time-SLIP sequence incorporating a variably positionable cine sub-sequence. The upper line in FIG. 2 depicts the R-wave of the subject's ECG (electrocardiogram) signal. As shown in FIG. 2, the MRI system 100 according to the exemplary embodiment applies inversion pulses A and/or B (e.g., 180° pulses), which are labeling RF pulses, after an initial trigger delay D1. The initial triggering delay D1 is usually short and may be close to zero. The gradient pulses are not shown explicitly in FIG. 2 to simplify the drawing. In addition, as shown in FIG. 2, the MRI system 100 according to the exemplary embodiment continues acquiring data by using the segmented cine sub-sequence during the duration D2. For example, the MRI system 100 according to the exemplary embodiment depicts 4 to 5 cine image frames effectively taken at sequential BBTI time intervals by continuing acquiring data by using the cine sub-sequence in a state where an RF pulse, SS (slice select) pulse, PE (phase encode) pulse, and RO (read out) pulse, etc are preferably initialized as having at least about 300-400 milliseconds covering at least the subject's diastole.

As depicted in FIG. 2, the initial BBTI delay interval D4 (e.g., approximately 600 milliseconds) is the delay from the initial triggering delay and is positioned as the beginning of the segmented cine sub-sequence. After the segmented cine sub-sequence and a further recovery time delay D3, the MRI system 100 according to the exemplary embodiment starts a subsequent data acquisition cycle (e.g., to allow the nuclear magnetization to return to a suitable starting condition).

In an exemplary embodiment, the operator or the MRI system 100 can select these time intervals such that they conform to a given subject's ECG signal. For example, the operator or the MRI system 100 may efficiently define the time intervals in the entire single sequence by selecting all or any three of D1, D2, D3 and D4. Alternatively, the operator or the MRI system 100 may define other time intervals as, for example, the initial setting value defined for the MRI system 100. In the exemplary embodiment, the operator or the MRI system 100 may can previously choose or preset whether to use the inversion pulse A and/or the inversion pulse B. When the MRI system 100 according to the exemplary embodiment uses the area non-selective inversion pulse A and the area selectable inversion pulse B, it can depict selectively-marked, or tagged, blood flow into the myocardium.

Figure 3:
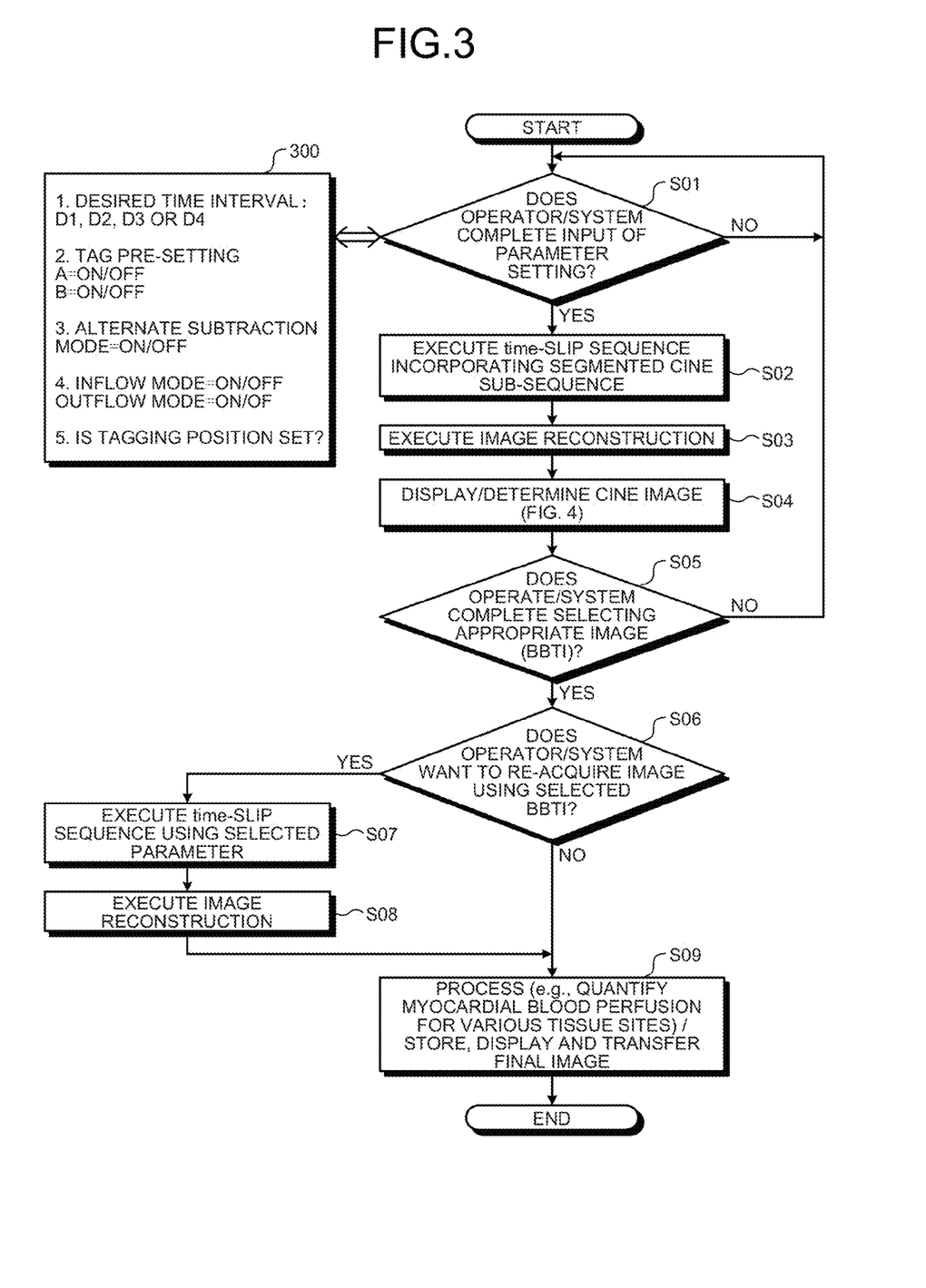
FIG. 3 is a flowchart depicting a procedure of a computer program code executed in the MRI system according to the exemplary embodiment.

FIG. 3 is a flowchart depicting a procedure of a computer program code executed by the MRI system 100 according to the exemplary embodiment. The MRI system 100 first determines whether the operator or the MRI system 100 has completed inputting a parameter setting (step S01). For example, the operator input is as represented by a GUI (graphical user interface) 300. For example, in the exemplary embodiment, the operator can select some of the time intervals D1, D2, D3 and D4 at step S01. The operator may select only one, two or three of these intervals, while the MRI system 100 may determine the remaining interval(s). If the length of the total time interval is known and, when there are n time intervals, then the operator or the MRI system 100 defines n−1 of the time intervals. The operator or the MRI system 100 can independently define tagging presets for both inversion pulses A and B, if desired (i.e., the operator or the MRI system 100 can presets on/off of each of the inversion pulses A and B). The operator or the MRI system 100 can also define on on/off alternate approach. The operator or the MRI system 100 can alternatively selects the flow-in mode or the flow-out mode so as to alternatively select the tagging position (e.g., upstream of the ROI or within the ROI). Some or all of these pulse sequence parameters may be selected by the MRI system 100 and/or selected by the operator via a suitable GUI.

When the pulse sequence parameter is defined at step S01 (YES step S01), the MRI system 100 executes the time-SLIP sequence incorporating the cine sub-sequence so as to acquire MR data (step S02). Suitable cine sub-sequences for use as the cine sub-sequence are known, per se. See, for example, US Patent Application Publication No. 2008/0061780 A1 (filed Sep. 10, 2007 and published Mar. 13, 2008) and/or Ser. No. 12/722,875 filed Mar. 12, 2010. Such cine sequences may also be referred to as segmented cine sequences (e.g., because such cine sequences may be segmented in at least k-space).

Figure 4:
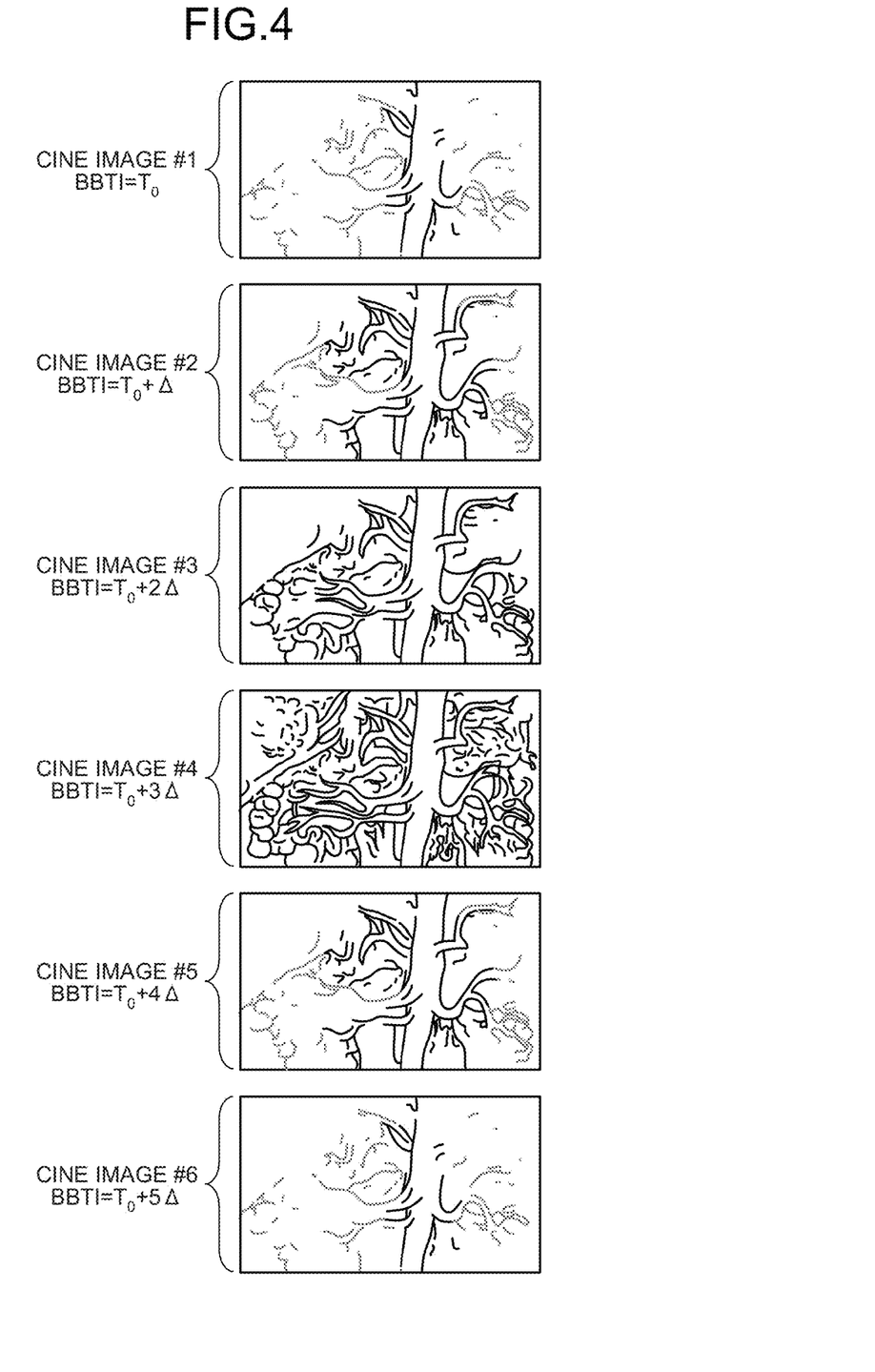
FIG. 4 is a diagram illustrating cine images according to the exemplary embodiment.

The MRI system 100 then executes a suitable image reconstruction processing (step S03). This image reconstruction processing includes alignment between images and the image subtraction process after the alignment. The MRI system 100 according to the exemplary embodiment then displays the acquired cine image frames as shown in FIG. 4. As is clear from FIG. 4, Frame 4 is the most clear among the successive cine images. Accordingly, the operator or the MRI system 100 can identify the BBTI time interval associated with that frame as an appropriate BBTI time interval. The identifying of an appropriate cine image frame and its corresponding BBTI time interval may be effected also by suitably-programmed computer processes without displaying the images to the operator (as is also indicated at step S04 in FIG. 3). At step S05, the MRI system 100 determines whether the operator or the MRI system 100 has identified an allowable and appropriate BBTI time interval (step S05). If not (NO at step S05), the MRI system 100 returns to step S01 to allow the operator or the MRI system 100 to input a parameter setting.

If an appropriate image and a BBTI interval has been identified (YES at step S05), the MRI system 100 determines whether there is an instruction from the operator or the MRI system 100 to, by using the identified BBTI time interval (e.g., possibly use of a 3D series of multi-slice data acquisition cycles may be desired), re-acquire an MRA image using a time-SLIP sequence (step S06). When it is determined to acquire MRA images using a time-SLIP sequence (YES at step S06), the MRI system 100 executes the time-SLIP sequence with the chosen parameters including the identified appropriate BBTI parameter (step S07). The MRI system 100 then executes image reconstruction, including required image subtraction processing and using known and preferable image alignment, for the MR data acquired at step S07 (step S08). When it is determined to acquire no MRA image using the time-SLIP sequence at step S06 (NO at step S06), the MRI system 100 (which has already used the appropriate BBTI value identified in fact) outputs the pre-chosen cine image frame as a final output image (step S09).

Regardless whether the final output image is the chosen cine image or the MRA image acquired with the new time-SLIP sequence by using the appropriate BBTI value, the MRI system 100 further processes the MRA image of the appropriate time-SLIP sequence. Alternatively, the MRI system 100 performs all or any of storing and displaying of the MRA image of the appropriate time SLIP sequence as well as transferring/exporting the MRA image to a remote facility/process/system (e.g., the MRI system 100 subtracts, by pixel-by-pixel basis, the magnitude of pixel values in one image from the magnitude of corresponding pixel values in another image and/or subtracts complex-valued pixels in one image from corresponding complex-valued pixels in another image so as to suitably quantify the myocardial blood flow for various tissue sites in accordance with procedures already known by those skilled in the art).

The MRI system 100 according to the above-described exemplary embodiment will be described again below. The MRI system 100 according to the exemplary embodiment includes a first imaging execution unit, an identifying unit, and a second imaging execution unit. After applying a labeling RF pulse to the blood flowing into the myocardium of the subject, the first imaging execution unit performs sequential imaging of an imaging area including the myocardium in each segment of a k-space for a given time interval. Accordingly, the first imaging execution unit acquires multiple non-contrast MR data for which the time intervals between labeling and acquiring data are different. The identifying unit identifies, on the basis of the acquired multiple MR data acquired by the first imaging execution unit, a time interval taken by the labeled blood to reach a given position in the imaging area. The second imaging execution unit sets the identified time interval as a corresponding parameter of a pulse sequence. After applying a labeling RF pulse to the blood flowing into the myocardium of the subject, the second imaging execution unit acquires non-contrast MR data by imaging the imaging area including the myocardium. For example, the MRI system controller 22 shown in FIG. 1 includes the first imaging execution unit, the identifying unit, and the second imaging execution unit (not shown) and, by controlling each unit of the MRI system, the above-described various functions can be effected.

Figure 5:
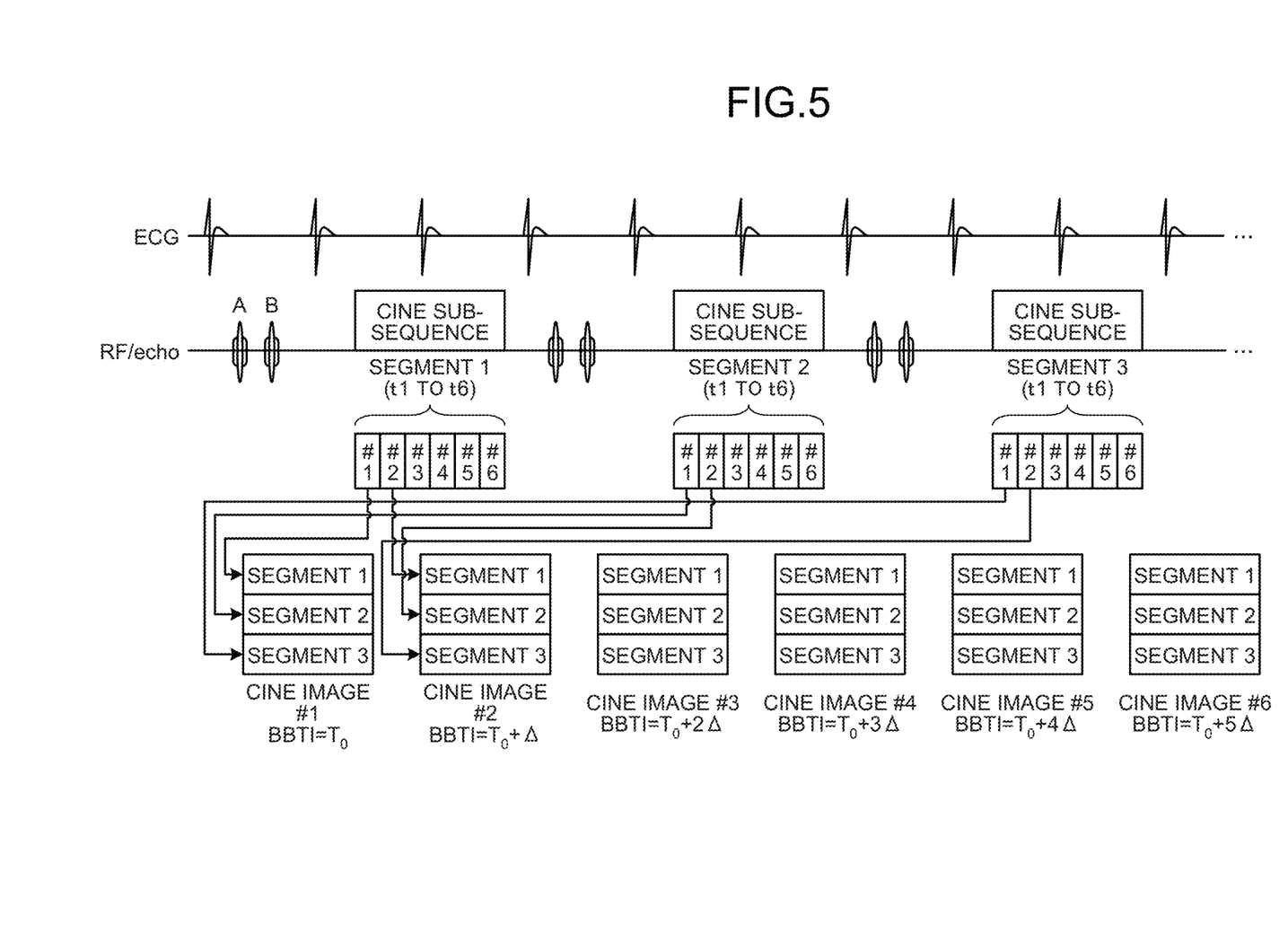
FIG. 5 is a diagram illustrating the time-SLIP sequence according to the exemplary embodiment.

The function of each unit will be described in detail using specific examples. First, the first imaging execution unit performs, for example, a time-SLIP sequence incorporating a segmented cine sub-sequence. FIG. 5 is a diagram illustrating the time-SLIP sequence according to the exemplary embodiment. As shown in FIG. 5, after a given delay has passed from the trigger regarding the cardiac phase (e.g, R-wave) of the subject, the first imaging execution unit applies inversion pulses A and B (or only an inversion pulse B).

Subsequently, the first imaging execution unit executes, for example, the cine sub-sequence using a segment k-space method in a given duration (denoted by the rectangle of "cine sub-sequence"). The segment k-space method is a data acquisition method of segmenting the k-space into multiple segments and sequentially acquiring k-space data in each segment. For example, it is assumed that the k-space is segmented into three segments as shown in FIG. 5. The first imaging execution unit acquires multiple MR data for which the BBTI time intervals are different with respect to Segment 1. The MR data acquired is k-space data of Segment 1 corresponding to cine images #1 to #6 as shown in FIG. 5. The first imaging execution unit acquires multiple MR data for which BTTI time intervals are different with respect to Segment 2. Furthermore, the first imaging execution unit acquires multiple MR data for which BBTI time intervals are different with respect to Segment 3. As described above, the first imaging execution unit acquires MR data for which BBTI time intervals are different with respect to every segment over multiple heart rates. In the exemplary embodiment, the first imaging execution unit performs sequential imaging during a given time interval including the diastole among the subject's cardiac phase.

On the basis of the multiple MR data acquired by the first execution unit, the identifying unit identifies a time interval taken by the labeled blood to reach a given position in the imaging area. Some methods are can be applied to the identifying process performed by the identifying unit. Methods 1 to 3 described below are nothing more than examples.

In Method 1, for example, the identifying unit generates multiple MRA (magnetic resonance angiography) images from the acquired MR data. In other words, the identifying unit reconstructs the multiple MR data acquired with respect to each segment and for which BBTI time intervals are different by consolidating them with respect to each BBTI value so that multiple MRA images for which BBTI time intervals are different are generated. In this case, because the identifying unit consolidates the MR data acquired over multiple heart rates into a single MRA image, it is preferable that alignment be performed. The identifying unit outputs the generated multiple MRA images to the display 24 and receives an input specifying a given MRA image from the operator.

Figure 6:
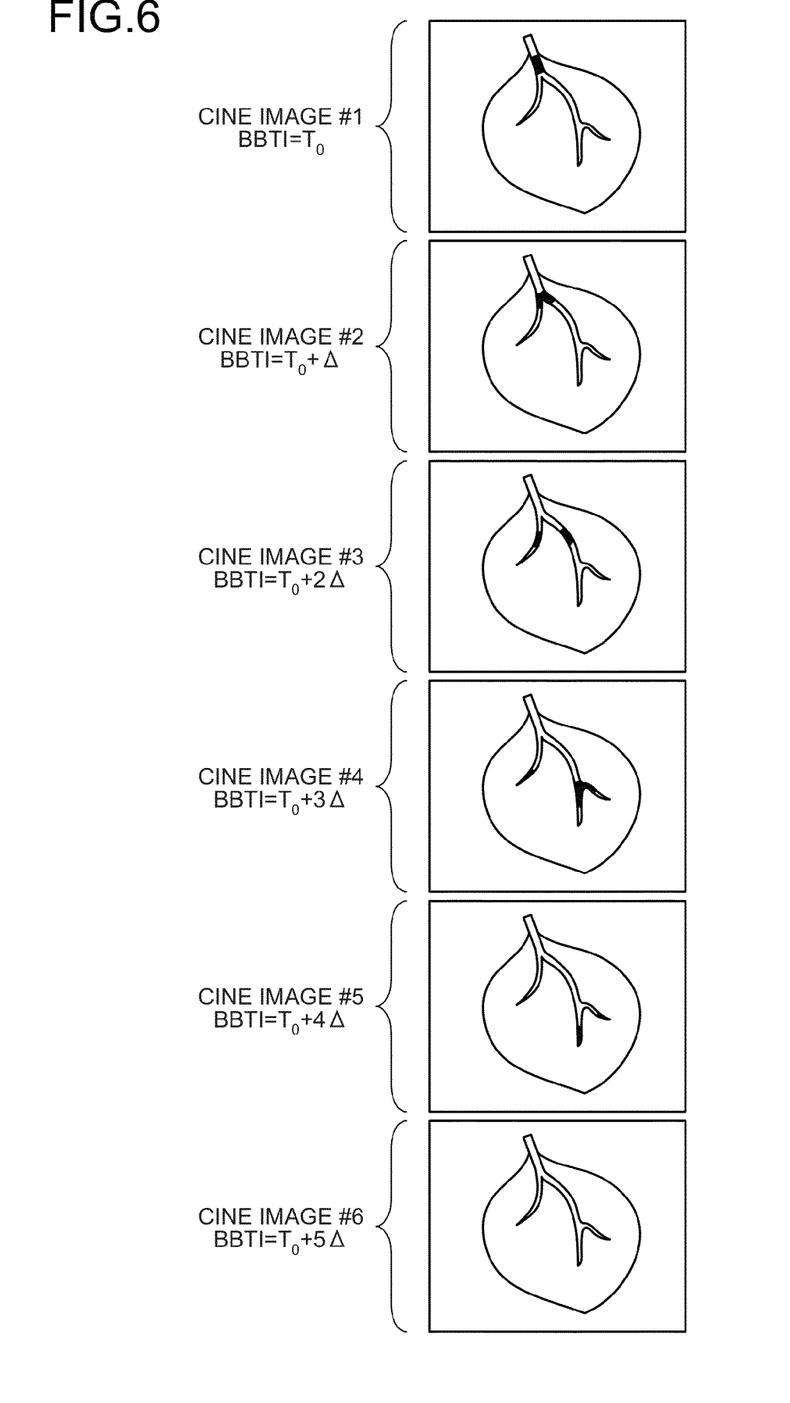
FIG. 6 is a diagram illustrating cine images according to the exemplary embodiment.

FIG. 6 is a diagram illustrating cine images according to the exemplary embodiment. For example, as shown in FIG. 6, the identifying unit outputs multiple MRA images for which BBTI time intervals are different (cine images #1 to #6) to the display 24. The operator then determines, for example, that Cine image #4 is an appropriate MRA image and makes an input specifying Cine image #4. The identifying unit receives the input and identifies, as a time interval taken by the labeled blood to reach the given position in the imaging area, a BBTI time interval (BBTI=$T_0+3\Delta$) corresponding to the specified MRA image. The "given position in the imaging area" is, for example, the position that a doctor who gives a diagnosis wants to actually observe and it can be set arbitrarily.

In Method 2, for example, the identifying unit analyzes signal values of the acquired multiple MR data and automatically identifies, on the basis of the result of the analysis results of the analyzed signal values, a time interval taken by the labeled blood to reach a given position in an imaging area. For example, after generating multiple MRA images for which BBTI time intervals are different, the identifying unit analyzes signal values of an area in each of the MRA images (for example, corresponding to the given position in the imaging area). The identifying unit determines the image with the highest signal value (or the image with lowest signal value) in the area and identifies the BBTI time interval corresponding to the image as a time interval taken by the labeled blood to reach the given position in an imaging area.

In Method 3, for example, the identifying unit analyzes the signal values of acquired multiple MR data and outputs the analysis result of the analyzed signal values to the display 24. For example, after generating multiple MRA images for which BBTI time intervals are different, the identifying unit analyzes signal values of an area in each of the MRA images (for example, corresponding to the given position in the imaging area). The identifying unit then outputs a graph depicting the pixel value transition in combination with the corresponding index of the MRA image. The operator then, for example, performs an input specifying the MRA image with the highest signal value. The identifying unit receives this input and identifies, as the time interval taken by the labeled blood to reach a given position in the imaging area, the BBTI time interval corresponding to the specified MRA image.

When the time interval taken by the labeled blood to reach a given position in the imaging area is identified, the second imaging execution unit sets the time interval identified by the identifying unit as the corresponding parameter of the pulse sequence. For example, the second imaging execution unit sets the time interval identified by the identifying unit as the BBTI value that is a parameter of a normal time-SLIP sequence not incorporating any cine sub-sequence. The second imaging execution unit executes this time-SLIP sequence and acquires MR data. For example, the first imaging execution unit acquires two-dimensional ME data and the second imaging execution unit acquires three-dimensional MR data.

As described above, in the MRI system 100 according to the exemplary embodiment, the first imaging execution unit performs imaging in order to apply an appropriate parameter (BBTI value) to imaging performed by the second imaging execution unit. In the above-described exemplary embodiment, because of the high temporal resolution of imaging performed by the first imaging execution unit, an appropriate parameter (BBTI value) can be selected and applied to the imaging performed by the second imaging execution unit. In other words, in the above-described exemplary embodiment, because the first imaging execution unit acquires MR data by using the segmented cine sub-sequences, the imaging temporal resolution is high. Circulation of an order of few msec to few tens of msec can be performed.

The MRI system 100 according to the exemplary embodiment receives a setting, made by the operator, of various parameters regarding the time-SLIP sequence executed by the first imaging execution unit or the parameters are automatically determined in the MRI system 100. In other words, the MRI system 100 according to the exemplary embodiment further includes a receiver that receives a setting of a parameter regarding the given time interval and the first imaging execution unit positions the given time interval on the time axis of the pulse sequence in accordance with the received setting of the parameter and executes sequential imaging. For example, the MRI system controller 22 shown in FIG. 1 includes the receiver (not shown).

For example, the receiver receives a setting of at least one of D1, D2, D3 and D4 described above using FIG. 2. As shown in FIG. 2, D1 is the time interval between the trigger (R-wave) regarding the subject's heart rate and application of the first RF pulse (inversion pulse A or inversion pulse B). D2 is the time interval of the given time interval. D3 is the time interval between the end of the given time interval and the start of the next cycle. D4 is the time interval between the first RF pulse (the inversion pulse A or inversion pulse B) and the start of the given time interval.

The reason why D3 is set will be described. As shown in FIG. 5, the time-SLIP sequence executed by the first imaging execution unit repeatedly executes a cycle including a given time interval (denoted by the rectangle of "cine sub-sequence" in FIG. 5). As described below, one MRA image is generated by consolidating each segment acquired in each cycle. Because the cardiac cycle of the subject is not necessarily constant, if MR data in each segment is acquired on the basis of only the elapsed time from the trigger (e.g., R-wave) regarding the subject's heart phase, for example, inconsistency occurs in the recovery of the vertical magnetic components between segments. Accordingly, the image quality of the MRA image generated by consolidating each segment also decreases. For this reason, in the exemplary embodiment, D3 that should be secured as a recovery time is set (or as an elapsed time after application of an inversion pulse). For example, when the next R-wave is detected before D3 is not secured yet, the first imaging execution unit does not acquire any MR data and waits until the next cycle. In contrast, when the next R-wave is detected after D3 is secured, the first imaging execution unit acquires MR data.

Figure 7:
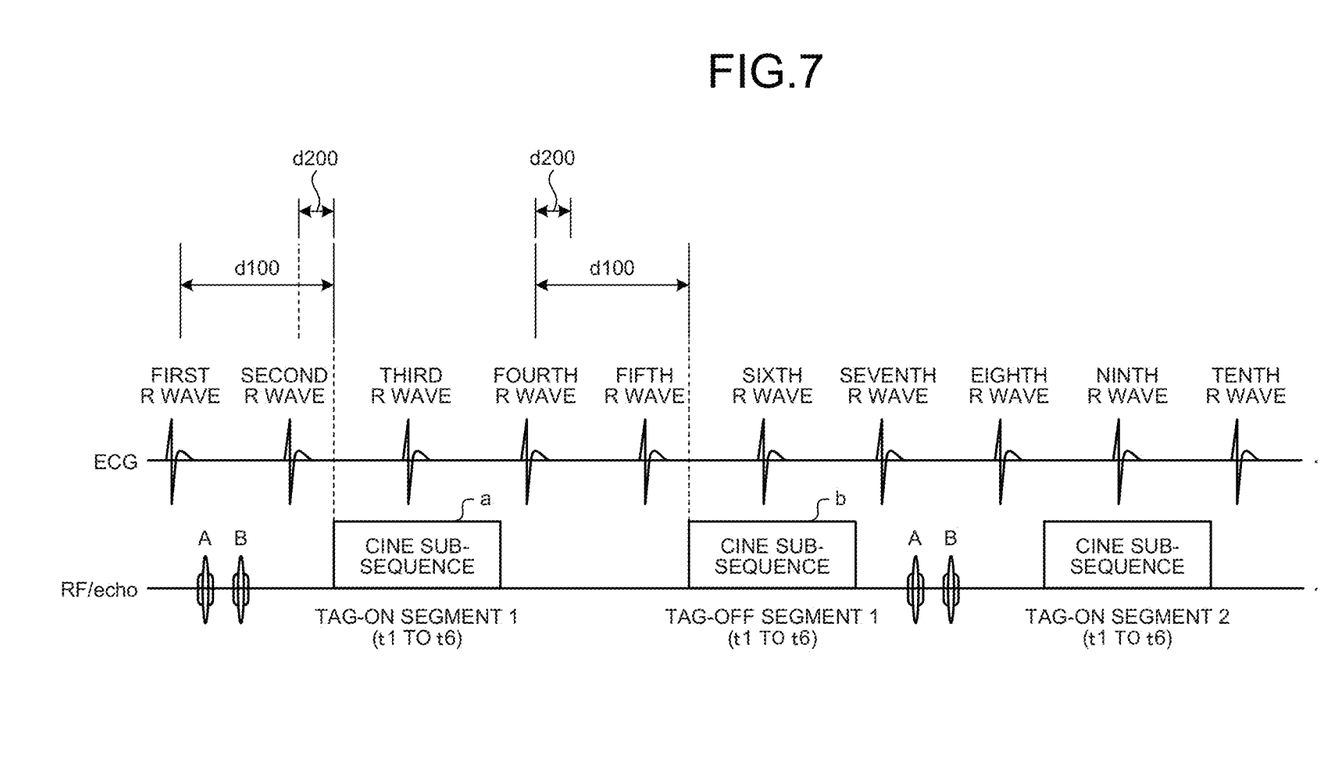
FIG. 7 is a diagram illustrating another example of the time-SLIP sequence according to the exemplary embodiment.

FIG. 7 is a diagram illustrating another example of the time-SLIP sequence according to the exemplary embodiment. For example, the first imaging execution unit may alternately turns on/off the inversion pulse as shown in FIG. 7. In this case, the first imaging execution unit applies an inversion pulse at a heart rate and then acquires multiple MR data for which BBTI time intervals are different with respect to Segment 1. The MR data acquired here is, like the case shown in FIG. 5, k-space data of Segment 1 corresponding to Cine images #1 to #6. The first imaging execution unit then, without applying any inversion pulse in another heart rate, acquires multiple MR data for which BBTI time intervals are different with respect to the same Segment 1. Thereafter, the first imaging execution unit next applies an inversion pulse at another heart rate and acquires multiple MR data for which BBTI time intervals are different with respect to Segment 2. As described above, the first imaging execution unit may alternately perform acquisition in which an inversion pulse is applied and acquisition in which no inversion pulse is applied.

A supplementary description will be given for the relationship between acquisition in which an inversion pulse is applied and acquisition in which no inversion pulse is applied. In the example of FIG. 7, the time interval between a first R wave and the start of a cine sub-sequence a in which acquisition is performed by applying an inversion pulse regarding Segment 1 is equal to the time interval between a fourth R-wave and the start of a cine sub-sequence b in which acquisition is performed regarding Segment 1 without applying any inversion pulse (d100 in FIG. 7). However, the exemplary embodiment is not limited to this. Because no inversion pulse is applied in the cine subsequence b, for example, the time interval between a second R-wave and the start of a cine sub-sequence a may be equal to the time interval between the fourth R-wave and the start of the cine sub-sequence b (d200 in FIG. 7). In other words, in this case, the cine sub-sequence b begins after the time d200 has passed after the fourth R-wave.

The exemplary embedment is not limited to a technique of alternately performing acquisition in which an inversion pulse is applied and acquisition in which no inversion pulse is applied. For example, for one image, acquisition in which no inversion pulse is applied may be collectively performed and then acquisition in which an inversion pulse is applied may be sequentially performed. For example, after acquisition in which no inversion pulse is applied is performed regarding Segments 1 to 3, acquisition in which an inversion pulse is applied may be successively performed with respect to each of the segments. Acquisition in which no inversion pulse is applied for one image is not necessarily performed at first, and it may be performed at desired timing (intermediate timing or last).

Figure 8:
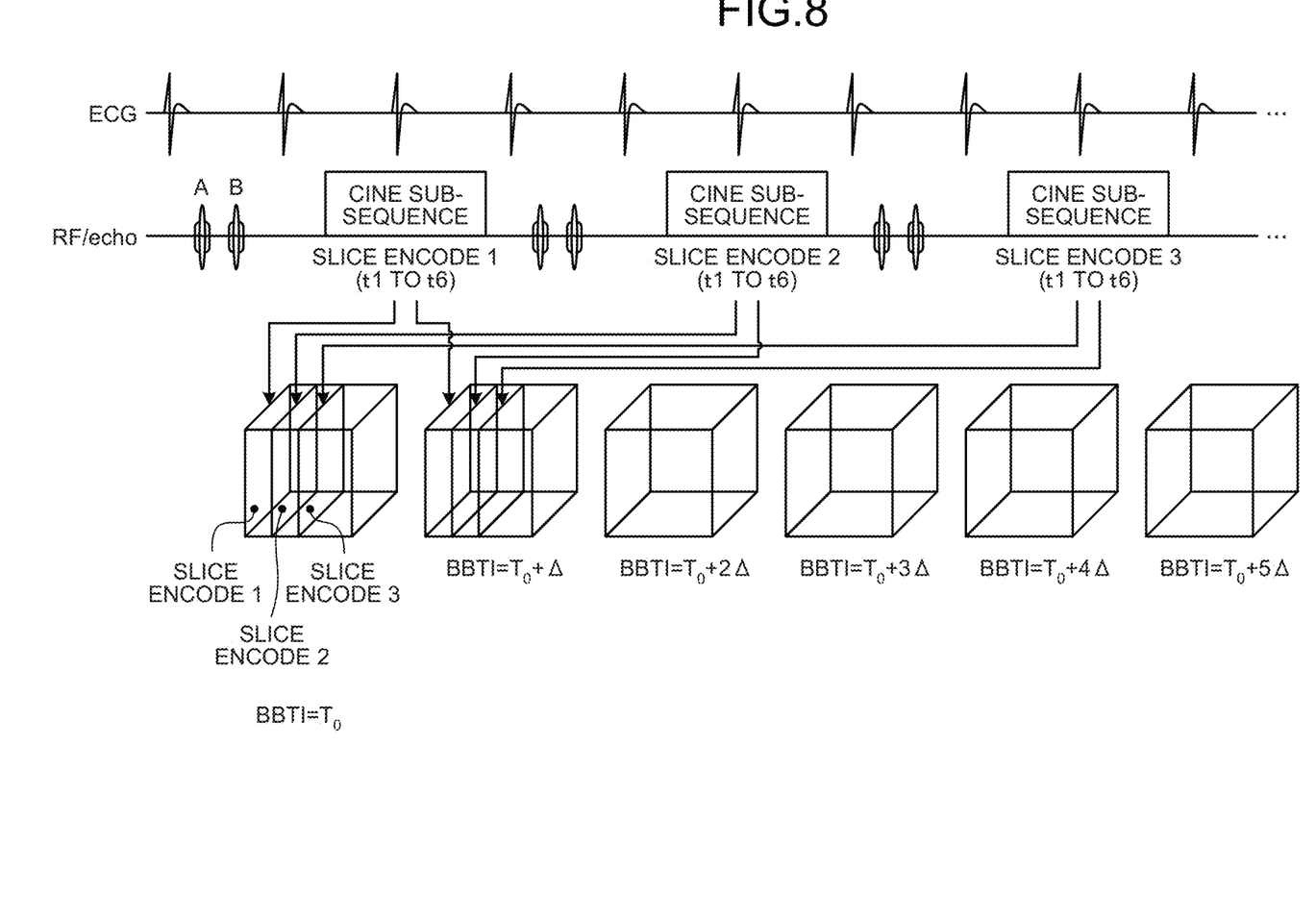
FIG. 8 is a diagram illustrating another example of the time-SLIP sequence according to the exemplary embodiment.

FIG. 8 is a diagram illustrating another example of the time-SLIP sequence according to the exemplary embodiment. For example, as shown in FIG. 8, the first imaging execution unit may acquire multiple three-dimensional data for which BBTI time intervals are different. For example, the first imaging execution unit acquires, at a heart rate, multiple MR data for which BBTI time intervals are different regarding Slice Encode 1 that is a segment of the three-dimensional data. The first imaging acquisition unit acquires, at another hart rate, acquires multiple MR data for which BBTI time intervals are different regarding Slice Encode 2. Although illustrations are appropriately omitted in FIG. 8, the first imaging execution unit acquires multiple MR data for which BBTI time intervals are different for cardiac phases over multiple heart rates for every slice encode.

Figure 9A:
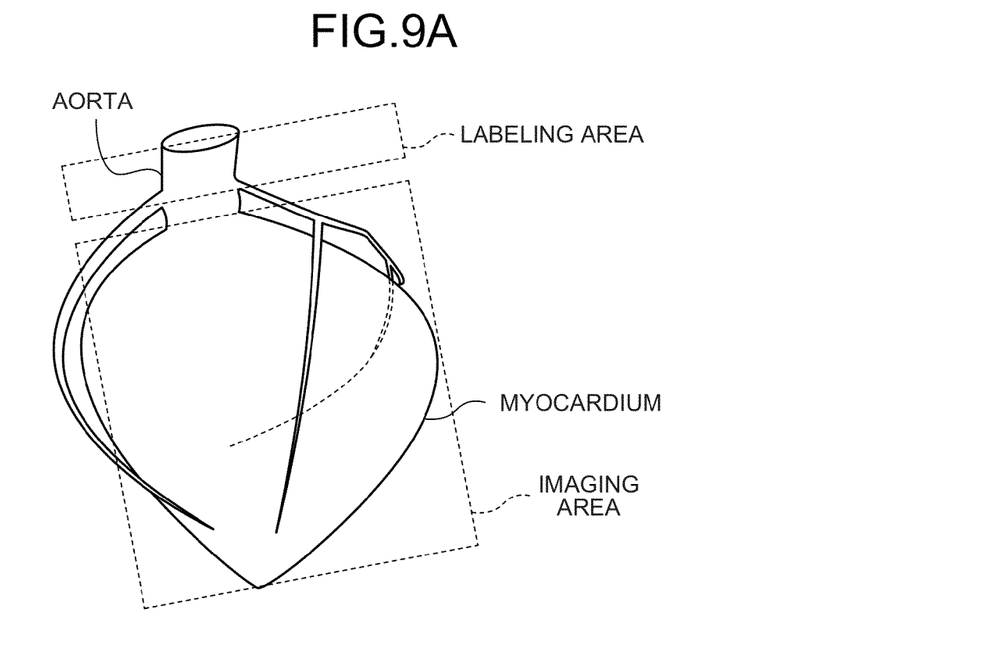
FIG. 9A is a diagram illustrating the relationship between a labeling area and an imaging area according to the exemplary embodiment.
Figure 9B:
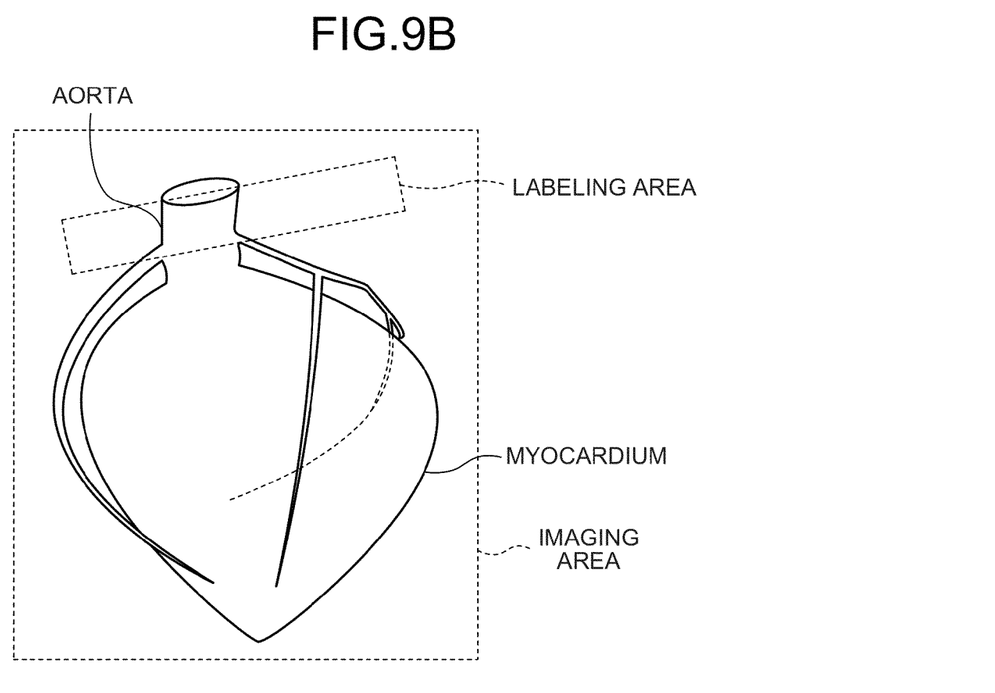
FIG. 9B is a diagram illustrating the relationship between the labeling area and the imaging area according to the exemplary embodiment.

Furthermore, the relationship between a labeling area and an imaging area according to the exemplary embodiment will be described below. FIGS. 9A and 9B are diagrams illustrating the relationship between a labeling area and an imaging area according to the exemplary embodiment.

FIG. 9A is a diagram illustrating flow-in angiography. In the exemplary embodiment, in the case of flow-in angiography, no inversion pulse A, which is an area non-selective inversion pulse, is not applied but only an inversion pulse B, which is an area selective inversion pulse, is applied. The inversion pulse B is applied to a labeling area that is set outside the imaging area and independent of the imaging area. As shown in FIG. 9A, the labeling area is set in the aorta positioned upstream of the myocardium. Application of an inversion pulse B to the labeling area inverts the vertical magnetic components of the blood in the labeling area. Accordingly, the blood in the labeling area is labeled and, in the imaging area, the signal value of the part that the blood reaches after the BBTI time interval decreases.

FIG. 9B is a diagram illustrating flow-out angiography. In the exemplary embodiment, in the case of flow-out angiography, both of an inversion pulse A, which is an area non-selective inversion pulse, and an inversion pulse, which is an area selective inversion pulse, are applied. The inversion pulse A is applied all over the imaging area. Because the inversion pulse A is applied all over the imaging area, the vertical magnetic components of the myocardium and blood in the labeling area are inverted. The inversion pulse B is then applied to the labeling area that is set outside the imaging area and independent of the imaging area. As shown in FIG. 9B, the labeling area is set in the aorta positioned upstream of the myocardium. Application of the inversion pulse B to the labeling area selectively inverts the vertical magnetic components of the blood in the labeling area after the recovery in the time interval between the inversion pulse A and the inversion pulse B. In this manner, the blood in the labeling area is labeled and, in the imaging area, the signal value of the part that the blood reaches after the BBTI time interval increases.

The definitions of flow-in angiography and flow-out angiography are not limited to the above-described definitions. By some definitions, they may be referred to as the opposite names or other names. Setting of an imaging area and a labeling area may be arbitrarily changed in accordance with the purpose of imaging. Furthermore, as application examples, the labeling method may be, for example, pCASL (pulsed continuous arterial spin labeling) in which an inversion pulse is successively applied.

According to the magnetic resonance imaging apparatus and the magnetic resonance imaging method according to at least one of the above-described exemplary embodiments, appropriate images of the blood flow in a cardiac muscle tissue can be acquired.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging apparatus comprising:
   a first imaging execution unit configured to, after applying a labeling RF (radio frequency) pulse to blood flowing into a myocardium of a subject, acquire multiple non-contrast MR (magnetic resonance) data for which the time intervals between labeling and acquiring data are different by performing sequential imaging of an imaging area including the myocardium in each segment of a k-space for a given time interval;
   an identifying unit configured to identify, on the basis of the acquired multiple MR data, a time interval taken by the labeled blood to reach a given position in the imaging area; and
   a second imaging execution unit configured to set the identified time interval as a corresponding parameter of a pulse sequence and, after applying a labeling RF pulse to the blood flowing into the myocardium of the subject, acquire non-contrast MR data by imaging the imaging area including the myocardium.

2. The magnetic resonance imaging apparatus according to claim 1, further comprising a receiver configured to receive a setting of the parameter regarding the given time interval,
wherein the first imaging execution unit positions the given time interval on a time axis of the pulse sequence in accordance with the received setting of the parameter and performs the sequential imaging.

3. The magnetic resonance imaging apparatus according to claim 2, wherein
the first imaging execution unit repeatedly executes the cycle including the given time interval,
the receiver receives, as the parameter regarding the given time interval, a setting of any one of a first time interval between a trigger regarding a cardiac phase of the subject and an application of a first RF pulse, a second time interval that is the duration of the given time interval, a third time interval between the end of the given time interval and the start of the next cycle, and a fourth time interval between the first RF pulse and the start of the given duration.

4. The magnetic resonance imaging apparatus according to claim 1, wherein the first imaging execution unit performs sequential imaging of the imaging area including the myocardium for the given time interval including diastole.

5. The magnetic resonance imaging apparatus according to claim 1, wherein
the first imaging execution unit acquires two-dimensional MR data, and
the second imaging execution unit acquires three-dimensional MR data.

6. The magnetic resonance imaging apparatus according to claim 1, wherein the identifying unit outputs multiple MRA (magnetic resonance angiography) images generated from the acquired multiple MR data to a display and, by receiving an input specifying a given MRA image from an operator, identifies a time interval between labeling and acquiring data corresponding to the specified MRA image as the time interval taken by the labeled blood to reach the given position in the imaging area.

7. The magnetic resonance imaging apparatus according to claim 6, wherein the identifying unit performs an alignment when generating the multiple MRA images from the acquired multiple MR data.

8. The magnetic resonance imaging apparatus according to claim 1, wherein the identifying unit identifies the time interval taken by the labeled blood to reach the given position in the imaging area on the basis of an analysis result of signal values analyzed from the acquired multiple MR data.

9. The magnetic resonance imaging apparatus according to claim 1, wherein the identifying unit outputs an analysis result of signal values analyzed from the acquired multiple MR data and, by receiving an input with respect to the analysis result from an operator, identifies the time interval taken by the labeled blood to reach the given position in the imaging area.

10. A magnetic resonance imaging method performed by a magnetic resonance imaging apparatus, the method comprising:
a first imaging execution step of, after applying a labeling RF pulse to blood flowing into a myocardium of a subject, acquiring multiple non-contrast MR data for which time intervals between labeling and acquiring data are different by performing sequential imaging of an imaging area including the myocardium in each segment of a k-space for a given time interval;
an identifying step of identifying, on the basis of the acquired multiple MR data, a time interval taken by the labeled blood to reach a given position in the imaging area; and
a second imaging execution step of setting the identified time interval as a corresponding parameter of a pulse sequence and, after applying a labeling RF pulse to the blood flowing into the myocardium of the subject, acquiring non-contrast MR data by imaging the imaging area including the myocardium.

* * * * *